United States Patent [19]

Thang et al.

[11] Patent Number: 5,830,966

[45] Date of Patent: Nov. 3, 1998

[54] CYCLOPOLYMERIZATION MONOMERS AND POLYMERS

[75] Inventors: San Hoa Thang, Clayton South; Ezio Rizzardo, Wheelers Hill; Graeme Moad, Kallista, all of Australia

[73] Assignees: E. I. du Pont de Nemours and Company, Wilmington, Del.; Commonwealth Scientific & Industrial Research Organisation, Campbell, Australia

[21] Appl. No.: 586,858

[22] PCT Filed: Jul. 29, 1994

[86] PCT No.: PCT/AU94/00433

§ 371 Date: Jan. 26, 1996

§ 102(e) Date: Jan. 26, 1996

[87] PCT Pub. No.: WO95/04026

PCT Pub. Date: Feb. 9, 1995

[30] Foreign Application Priority Data

Jul. 30, 1993 [AU] Australia .................................. PM0280

[51] Int. Cl.⁶ .............................. C08F 22/12; C08F 14/00; C08F 20/42; C08F 20/54; C08F 20/04; C08F 16/36; C07C 255/00

[52] U.S. Cl. ..................... 526/321; 526/297; 526/303.1; 526/318.3; 526/316; 526/291; 558/462; 560/205; 562/595; 562/598; 564/204

[58] Field of Search ..................... 526/321, 291, 526/297, 303.1, 316, 318.3; 558/462; 560/205; 562/595, 598; 564/204

[56] References Cited

U.S. PATENT DOCUMENTS 4,322,491  3/1982  Sander et al. .......................... 430/286

FOREIGN PATENT DOCUMENTS 481733  8/1929  Germany .
2952697 A1  2/1981  Germany .................................. 16/36

OTHER PUBLICATIONS

Ronald Grigg, Paul Stevenson, and Tanachat Worakun, J. Chem. Soc., Chem. Commun., 1985, pp. 971–972.

Ronald Grigg, Paul Stevenson, and Tanachat Worakun, Tetrahedron 44(7), 2049–2054, 1988.

Akira Tanaka, Toshiaki Nakata, and Kyohei Yamashita Agr. Biol. Chem. 37(10), 2365–2371, 1973.

Takashi Tsuda and Lon J. Mathias, Macromolecules 26, 6359–6363, 1993.

Grigg, Ronald, et al., *The Regioselectivity of Rhodium and Palladium–Catalysed Cyclisations of 2–Bromo–1,6–and–1, 7–Dienes:* Tetrahedron 44(7), 2033–48, 1988.

Grigg, Ronald et al., "Regioselectivity Formation of 1,3–Dienes by the Palladium–Catalysed Intra–and Inter–Molecular Coupling of Vinyl Halides": Tetrahedron 44(7), 2049–54, 1988.

Grigg, Ronald, et al., "Palladium Catalysed Intra–and Inter–molecular Couplings of Vinyl Halides Regiospecific Formation of 1,3–Dienes": J. Chem. Soc. Chem. Commun. 14, 971–2, 1985.

Ahmar, Mohammed, et al. "Carbopalladation of Allenic Hydrocarbons. A New Way to Functionalized Styrenes and 1,3–Butadienes": Tetrahedron 43(3), 513–526, 1987.

de Groot, Ae, et al. "C–Alkylation of cyclic 1,3–diketones" Journal of the Royal Netherland Chemical Society 93(6), 153–155 1974.

Eglinton, R.A. et al. "Rearrangement of Diacetylenes to Aromatic Compounds"; Journal of the Chemical Society 1964, pp. 2597–2603.

*Primary Examiner*—Jeffrey T. Smith
*Assistant Examiner*—Wu C. Cheng
*Attorney, Agent, or Firm*—James A. Costello

[57] ABSTRACT

Compounds of general formula (I)

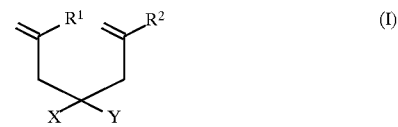

characterised in that $R^1$ and $R^2$ are independently selected from the group consisting of COOR, CN, aryl, substituted aryl, COOH, halogen, C(O)NHR⁴, C(O)NR⁵R⁶;

X and Y are independently selected from the group consisting of H, COOH, COOR, CN, R³CO—, C(O)NHR⁴, C(O)NR⁵R⁶, P(O)(OR⁷)₂ and SO₂R⁸; with the proviso that X and Y are not both H; or X and Y together with the carbon atom to which they are attached form a carbocyclic or heterocyclic ring system which can contain oxygen, sulfur or nitrogen atoms; and R, R³, R⁴, R⁵, R⁶, R⁷ and R⁸ are various groups;

and polymers and copolymers derived from such compounds.

9 Claims, No Drawings

CYCLOPOLYMERIZATION MONOMERS AND POLYMERS

This invention relates to new cyclopolymerisation monomers and to polymers and copolymers derived from such monomers. More specifically, the invention relates to new 4,4-disubstituted 1,6-diene monomers which are capable of undergoing polymerisations via an alternating intramolecular-intermolecular chain propagation. Polymers and copolymers derived from these monomers are also new and form a part of the invention.

Accordingly the present invention provides compounds of the general formula (I)

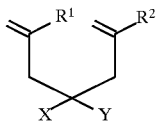

wherein
- $R^1$ and $R^2$ are independently selected from the group consisting of COOR, CN, aryl, substituted aryl, COOH, halogen, C(O)NHR$^4$, C(O)NR$^5$R$^6$;
- X and Y are independently selected from the group consisting of H, COOH, COOR, CN, R$^3$CO—, C(O)NHR$^4$, C(O)NR$^5$R$^6$, P(O)(OR$^7$)$_2$ and SO$_2$R$^8$; with the proviso that X and Y are not both H when $R^1$ and $R^2$ are both COOCH$_3$ or both phenyl; or X and Y together with the carbon atom to which they are attached form a carbocyclic or heterocyclic ring system which may contain oxygen, sulfur or nitrogen atoms;
- R is selected from the group consisting of $C_1$ to $C_{18}$ alkyl; $C_2$ to $C_{18}$ alkenyl; $C_2$ to $C_{12}$ alkynyl; $C_5$ to $C_8$ cycloalkyl; or any of the above substituted with a substituent selected from the group consisting of hydroxy, amino, azido, cyano, nitro, aldehyde, thioether, sulfonyl, cyanato, isocyanato, thiocyanato, isothiocyanato, epoxy, silyl, silyloxy, aziridine, acyloxy, carboxy, ester, carbamoyl, carbonyldioxy, urethane, ureylene, carbonyl, $C_1$ to $C_6$ dialkoxyphosphoryl, $C_1$ to $C_6$ dialkoxythiophosphoryl, tri($C_1$ to $C_6$ alkoxy)silyl, $C_1$ to $C_6$ alkoxy, phenyl; substituted aryl, halogen, —[(CH$_2$)$_m$O]$_n$—H and —[(CH$_2$)$_m$O], $_n$-alkyl where m and n are integers; or any combinations of any of the above groups; any of which groups or combinations may be reacted upon in a pre- or post-polymerisation step to further modify their functionality;
- $R^3$ is a $C_1$ to $C_6$ alkyl group, a cycloalkyl group or a substituted aryl group;
- $R^4$ is selected from the group consisting of H, $C_1$ to $C_{\_}$alkyl, $C_2$ to $C_{18}$ alkenyl, $C_2$ to $C_{12}$ alkynyl, $C_5$ to $C_8$ cycloalkyl; or any of the above substituted with a substituent selected from the group consisting of hydroxy, amino, azido, cyano, cyanato, isocyanato, epoxy, silyl, silyloxy, carboxy, ester, carbamoyl, $C_1$ to $C_6$ alkoxy, phenyl, substituted aryl and halogen; or any combinations of any of the above groups; any of which groups or combinations may be reacted upon in a pre- or post-polymerisation step to further modify their functionality;
- $R^5$ and $R^6$ are independently selected from $C_1$ to $C_{18}$ alkyl, $C_3$ to $C_8$ cycloalkyl, aralkyl and alkylaryl;
- $R^7$ is selected from the group consisting of H, $C_1$ to $C_{18}$ alkyl; and
- $R^8$ is selected from the group consisting of $C_1$ to $C_{18}$ alkyl, aryl or substituted aryl.

When X and Y form a ring system, suitable ring systems include a dimedone ring, a 1,3-dioxan-4,6-dione ring, a barbituric acid ring, a 3-alkyl-isoxazol-5(4H)-one ring or a 3-aryl-isoxazol-5(4H)-one ring.

The term "substituted aryl" is used herein to mean an aryl group that contains one or more substituents that do not interfere with the polymerisation process. Such substituents include alkyl, hydroxy, amino, ester, acid, acyloxy, amide, nitrile, haloalkyl, alkoxy, silyl or silyloxy groups.

Preferably the aryl group is a phenyl group. The preferred halogen atoms are Cl and Br.

The "parent" compound, 2,6-dicarbomethoxy-1,6-heptadiene (1) [formula (I); X=Y=H; $R^1$=$R^2$=COOCH$_3$] is known and has been studied under free radical cyclopolymerisation conditions by Marvel et al. (see: C. S. Marvel, R. D. Vest, *J. Amer. Chem. Soc.*, 1957, 79, p.5771). Recently, Choi et al. have reported the cyclopolymerisation of the parent compound using group-transfer polymerisation (see: S. K. Choi et al., *Macromolecules*, 1991, 24, p.5006–8). The synthetic route to the parent compound therein is quite difficult but it has been prepared by a multi-step synthesis in a moderate (about 50%) yield.

In contrast to this, the synthetic method to compounds of formula (I), as defined above, is very straightforward and all compounds can be synthesised from readily available starting materials, and in high yields.

The compounds of Formula (I) when $R^1$ and $R^2$ are the same may be optimally synthesised by reaction of a compound of formula (V) with two or more molar equivalents of a compound of formula (VI) in the presence of an organic or inorganic base.

Compounds of Formula (I) where $R^1$ and $R^2$ are different are synthesised by a two step procedure wherein approximately equimolar quantities of compounds of Formula (V) and (VI) are reacted together in the presence of an organic or inorganic base followed by reaction of the product with a compound of formula (VII) in the presence of an organic or inorganic base.

For example, the cyclopolymerisable monomer 2,4,4,6-tetrakis(ethoxycarbonyl)-1,6-heptadiene (2) [formula (I); $R^1$=$R^2$=X=Y=COOEt] was synthesised in 87% yield by a one-step reaction between diethyl malonate and ethyl 2-(bromomethyl)propenoate [obtained from a modified procedure of S. E. Drewes, G. Loizou and G. H. P. Roos, *Synthetic Communications*, 1987, 17(3), 291–298] in the presence of sodium hydride in acetonitrile.

The monomers of formula (I) readily undergo homo- or co-polymerisation. For example, free radical homopolymerisation of the monomer just described takes place in o-xylene with AIBN as initiator, with a yield of 91% after 64 hours. NMR ($^1$H and $^{13}$C) analyses display no residual olefinic resonances, and the NMR spectra of the cyclopolymer is consistent with structure (II) shown below.

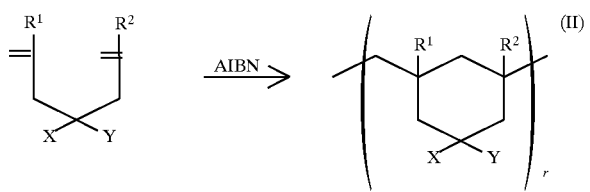

(where $R^1=R^2=X=Y=COOEt$)

The homopolymers are soluble in dichloromethane, chloroform, ethyl acetate, acetone, toluene, o-xylene, and the like but are insoluble in n-hexane and n-pentane (which can be used as non-solvents to precipitate the polymers).

The monomers/polymers of the invention provide the possibility of obtaining polymers with higher Tg and perhaps lower mass loss (more thermally stable due to the ring structure) compared to the corresponding poly(alkyl methacrylates). There is also the possibility of reducing polymerisation shrinkage (see: J. W. Stansbury, *J. Dent. Res.*, 1990, 69, p. 844–848).

The acrylate ester groups (or other groups $R^1$ and $R^2$) and the 4-substitutents (X, Y) can be selected to provide polymers having desired physical and chemical properties. Thus the invention provides monomers and polymers having the following potential applications:

New functional monomers and functional polymers.

Monomers with decreased volume shrinkage during polymerisation.

Thermally stable polymers.

Hydrophobic-hydrophilic polymers of the following structure:

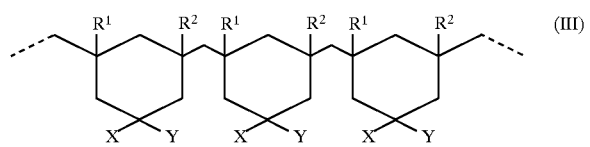

where for example the groups $R^1$ and $R^2$ may be hydrophilic groups, and X and Y may be hydrophobic groups (or vice versa).

The monomers (I) can also be copolymerised with known monomers. Such monomers may include, for example, acrylic monomers, styrene monomers and acrylamide monomers. Examples of such monomers are acrylic acid, methacrylic acid, methyl acrylate, ethyl acrylate, n-butyl acrylate, t-butyl acrylate, 2-ethylhexyl acrylate, methyl methacrylate, ethyl methacrylate, n-butyl methacrylate, ethyl triethyleneglycol methacrylate, 2-ethylhexyl methacrylate, n-dodecyl acrylate, n-dodecyl methacrylate, 1-tetradecyl methacrylate, 1-hexadecyl acrylate, 1-hexadecyl methacrylate, n-octadecyl acrylate, n-octadecyl methacrylate, tetrahydrofurfuryl acrylate, tetrahydrofurfuryl methacrylate, tetrahydropyranyl methacrylate, phenyl acrylate, benzyl acrylate, cyclohexyl methacrylate, phenyl methacrylate, benzyl methacrylate, 2-cyanoethyl acrylate, 2-hydroxyethyl acrylate, 2-hydroxyethyl methacrylate, hydroxypropyl acrylate, hydroxypropyl methacrylate, 2,3-dihydroxypropyl acrylate, 2,3-dihydroxypropyl methacrylate, poly(ethylene glycol)(n) monomethacrylate with n=200 and 400, poly (ethylene glycol)(n) monomethyl ether monomethacrylate with n=200; 400 and 1000, 2-isocyanatoethyl acrylate, 2-isocyanatoethyl methacrylate, glycidyl acrylate, glycidyl methacrylate, 2-sulfoethyl methacrylate, 3-sulfopropyl acrylate, 2,2,2-trifluoroethyl acrylate, 2,2,2-trifluoroethyl methacrylate, styrene, α-methylstyrene, 4-cyanostyrene, 4-chlorostyrene, chloromethylstyrene, vinylpyridine, vinyl carbazole, vinylidene halides, acrylonitrile, methacrylonitrile, acrylamide, methacrylamide, N-benzylacrylamide, N-hydroxymethylacrylamide, hydroxymethyldiacetoneacrylamide, N-(2-hydroxypropyl)-methacrylamide, vinyl acetate, and N-vinylpyrrolidone.

The invention is further described and illustrated by reference to the following non-limiting examples.

SYNTHESIS OF MONOMERS

Example 1

2,4,4,6-Tetrakis(ethoxycarbonyl)-1,6-heptadiene (2)

[Formula (I); $R^1=R^2=X=Y=COOEt$]

To a cooled suspension of sodium hydride (1.35 g, 45 mmol, 80% dispersion in oil) in acetonitrile (50 mL) was added diethyl malonate (3.20 g, 20 mmol). The resulting mixture was allowed to stir at 4° C. for 15 minutes before a solution of ethyl 2-(bromomethyl)propenoate (7.72 g, 40 mmol) in acetonitrile (10 mL) was added. The reaction mixture was then stirred at room temperature for 2 hours. Saturated sodium chloride solution (50 mL) was added and the mixture extracted three times with diethyl ether (200 mL in total). The combined organic phase was washed with water, then brine. After being dried over anhydrous sodium sulphate, filtered, and evaporated to dryness, the title compound (2) was obtained (7.05 g, 92% yield). $^1$H-NMR (CDCl$_3$) δ(ppm) 1.20 (t, 6H), 1.25 (t, 6H), 2.95 (s, 4H), 4.10 (q, 4H), 4.15 (q, 4H), 5.65 (s, 2H) and 6.25 (s, 2H).

Example 2

2,6-Diethoxycarbonyl-4,4-di-t-butoxycarbonyl-1,6-heptadiene (3),

[Formula (I); $R^1=R^2=COOEt$; $X=Y=COOC(CH_3)_3$]

This compound was prepared using a similar procedure to that described above in Example 1, with di-t-butyl malonate used instead of diethyl malonate. The title compound (3) was obtained in 90% yield. $^1$H-NMR (CDCl$_3$) δ(ppm) 1.27 (t, 6H), 1.45 (s, 18H), 2.95 (s, 4H), 4.20 (q, 4H), 5.70 (s, 2H) and 6.25 (s, 2H).

Example 3

2,2-Dimethyl-5,5-bis(2-ethoxycarbonyl-2-propenyl)-1,3-dioxan-4,6-dione (4)

[Formula (I); $R^1=R^2=COOEt$; X,Y as Meldrum's acid (2,2-dimethyl-1,3-dioxan-4,6-dione) ring]

To a stirred solution of Meldrum's acid (2,2-dimethyl-1,3-dioxan-4,6-dione; isopropylidene malonate) (1.44 g, 10 mmol) in chloroform (15 mL), dried potassium carbonate (4.15 g, 30 mmol) and cetyltrimethylammonium bromide (10.93 g, 30 mmol) were added. Then, a solution of ethyl 2-(bromomethyl)propenoate (3.86 g, 20 mmol) in chloroform (15 mL) was added dropwise. The resulting mixture was stirred at room temperature for 16 hours. Water (20 mL) was then added, the organic layer was separated, and the aqueous layer was extracted with chloroform (3×30 mL). The combined organic phase was then dried over anhydrous magnesium sulphate, filtered and evaporated to dryness, to give the title compound (4) in 83% yield. $^1$H-NMR (CDCl$_3$) δ(ppm): 1.25 (t, 6H); 1.75 (s, 6H); 3.10 (s, 4H); 4.15 (q, 4H); 5.70 (s, 2H) and 6.30 (s, 2H). $^{13}$C-NMR (CDCl$_3$) δ(ppm): 14.0, 29.3, 39.1, 54.0, 61.2, 107.0, 129.9, 135.1, 167.0 and 168.0.

Example 4

4,4-Di-t-butoxycarbonyl-2,6-diphenyl-1,6-heptadiene (5)

[Formula (I); $R^1=R^2=Ph$, $X=Y=COOC(CH_3)_3$]

To a stirred suspension of sodium hydride (0.20 g) in acetonitrile (15 mL) was added di-t-butyl malonate (0.55 g). The mixture was allowed to stir at room temperature for 15 minutes, then a solution of α-(bromomethyl)styrene (100 g) in acetonitrile (5 mL) was added and stirred for 3 hours. Water (20 mL) was added and the mixture extracted with ethyl acetate (50 mL). The combined organic layer was then dried over anhydrous magnesium sulphate, filtered and evaporated to dryness. After chromatography on a silica-gel column using 10% ethyl acetate in n-hexane as eluent, the pure title compound (5) was obtained (0.82 g, 72%). The product solidified on standing. $^1$H-NMR (CDCl$_3$) δ(ppm) 1.35 (s, 18H), 3.10 (s, 4H), 5.15 (s, 2H), 5.25 (s, 2H) and 7.20 (m, 10H).

Example 5

2,6-Dibenzyloxycarbonyl-4,4-di-t-butoxycarbonyl-1,6-heptadiene (6)

[Formula (I); $R^1=R^2=COOCH_2C_6H_5$; $X=Y=COOC(CH_3)_3$]

To a cooled suspension of sodium hydride (5.12 g, 0.17 mol, 80% dispersion in oil) in acetonitrile (300 mL), was added di-t-butyl malonate (14.78 g, 0.0684 mol). The resulting mixture was stirred at 4° C. for 15 minutes before a solution of benzyl 2-(bromomethyl)propenoate (34.90 g, 0.137 mol) in acetonitrile (100 mL) was added. The reaction mixture was then stirred at room temperature for 2 hours. Saturated sodium chloride solution (200 mL) was added and the mixture extracted three times with diethyl ether (600 mL in total). The combined organic phase was washed with water, then brine. After being dried over anhydrous sodium sulfate, filtered, evaporated to dryness and subjected to chromatography on a silica-gel column (Merck 60, 70–230 mesh; 10% diethyl ether in petroleum spirit as eluent) the title compound (6) was obtained (16.90 g, 44%) as a thick colourless liquid. $^1$H-NMR (CDCl$_3$) δ(ppm): 1.45 (s, 18H); 2.98 (s, 4H); 5.15 (s, 4H); 5.75 (s, 2H); 6.30 (s, 2H) and 7.35 (br. s, 10H).

Note: Benzyl 2-(bromomethyl)propenoate was obtained by the bromination reaction of the Baylis-Hillman reaction product of benzyl acrylate and paraformaldehyde in the presence of DABCO. $^1$H-NMR data for benzyl 2-(bromomethyl)propenoate: δ(ppm) (CDCl$_3$) 4.20 (s, 2H); 5.25 (s, 2H); 6.00 (s, 1H); 6.40 (s, 1H) and 7.40 (br.s, 5H).

Example 6

4,4-Dibenzyloxycarbonyl-2,6-di-t-butoxycarbonyl-1,6-heptadiene (7)

[Formula (I); $R^1=R^2=COOC(CH_3)_3$; $X=Y=COOCH_2C_6H_5$]

The starting material, t-butyl 2-(bromomethyl)propenoate was obtained by bromination of the product from the Baylis-Hillman reaction of t-butyl acrylate and paraformaldehyde in the presence of DABCO.

To a cooled suspension of sodium hydride (2.02 g, 0.056 mol, 80% dispersion in oil) in acetonitrile (150 mL), was added dibenzyl malonate (7.98 g, 0.028 mol). The resulting mixture was stirred at 4° C. for 15 minutes before a solution of t-butyl 2-(bromomethyl)propenoate (12.41 g, 0.056 mol) in acetonitrile (20 mL) was added. The reaction mixture was then stirred at room temperature for 2 hours. Water (250 mL) was added and the mixture stirred vigorously at room temperature. The title product (7) precipitated out and was collected by filtration (15.80 g, ~100%) and allowed to air dry. The pure product (7) can be obtained after recrystallisation from dichloromethane (or chloroform) into methanol, m.p. 108°–109° C. $^1$H-NMR (CDCl$_3$) δ(ppm): 1.48 (s, 18H), 3.00 (s, 4H); 5.08 (s, 4H); 5.58 (s, 2H); 6.17 (s, 2H) and 7.25 (br.s, 10H). $^{13}$C-NMR (CDCl$_3$) δ(ppm): 28.0, 34.7, 57.7, 67.2, 80.7, 127.9, 128.1, 128.4, 135.4, 137.3, 166.2 and 170.1.

Example 7

4,4-Dibenzyloxycarbonyl-2,6-dibromo-1,6-heptadiene (8)

[Formula (I); $R^1=R^2=Br$; $X=Y=COOCH_2C_6H_5$] (Not included in the invention)

To a suspension of sodium hydride (0.66 g, 0.022 mol, 80% dispersion in oil) in acetonitrile (25 mL), was added at room temperature dibenzyl malonate (3.10 g, 0.011 mol) in acetonitrile (5 mL). Then a solution of 2,3-dibromopropene (4.36 g, 0.022 mol) in acetonitrile (5 mL) was added slowly under nitrogen also at room temperature. The reaction mixture was allowed to stir overnight (~16 hr). Water (100 mL) was added and the mixture extracted three times with diethyl ether (total 150 mL). The combined organic layer was washed once with saturated sodium chloride solution (40 mL) and then dried over anhydrous sodium sulphate. After filtration and evaporation to dryness, the crude product (8) (~100%) was obtained as a brownish oil. $^1$H-NMR (CDCl$_3$) δ(ppm): 3.35 (s, 4H), 5.10 (s, 4H); 5.58 (s, 2H); 5.70 (s, 2H) and 7.30 (m, 10H).

Example 8

2,4,4-Tri(ethoxycarbonyl)-6-phenyl-1,6-heptadiene (9)

[Formula (I); $R^1=Ph$; $X=Y=R^2=COOEt$]

To a suspension of sodium hydride (70 mg, 80% dispersion in oil) and ethyl 2,4-bis(ethoxycarbonyl)-pent-4-enoate [obtained from the reaction between equimolar diethyl malonate and ethyl 2-(bromomethyl)propenoate] (544 mg, 2 mmol) in acetonitrile (5 mL) was added a solution of α-(bromomethyl)styrene (400 mg, 2 mmol) in acetonitrile (5 mL). The reaction mixture was allowed to stir at room temperature for 16 hours. Water (20 mL) was added, the mixture extracted three times with diethyl ether (3×20 mL). The combined organic layer was then washed once with saturated sodium chloride solution, dried over anhydrous magnesium sulfate, filtered, and evaporated to dryness, to give the crude product (760 mg, 98%) as a thick oil. The title compound (9) (560 mg, 72%) was obtained after purification by column chromatography on a short column of silica-gel using diethyl ether:petroleum spirit 40°–60° C. (1:4) as eluent. $^1$H-NMR (CDCl$_3$) δ(ppm): 1.17 (t, 6H); 1.26 (t, 3H); 2.90 (s, 2H); 3.18 (s, 2H); 3.85 (m, 4H); 4.15 (q, 2H); 5.18 (s, 1H); 5.25 (s, 1H); 5.62 (s, 1H); 6.20 (s, 1H) and 7.30 (m, 5H).

Example 9

4-Cyano-2,4,6-tris(ethoxycarbonyl)-1,6-heptadiene (10)

[Formula (I); $R^1=R^2=X=COOEt$; $Y=CN$]

To a suspension of sodium hydride (1.35 g, 0.045 mol, 80% dispersion in oil) in acetonitrile (50 mL) was added a solution of ethyl cyanoacetate (2.26 g, 0.02 mol) in acetonitrile (10 mL) at room temperature with vigorous stirring. The resulting mixture was stirred for 10 minutes before a solution of ethyl 2-(bromomethyl)propenoate (7.72 g, 0.04 mol) in acetonitrile (20 mL) was added and allowed to stir further at room temperature overnight (16 h). This reaction was initially exothermic. Water (50 mL) was added, and the mixture extracted three times with diethyl ether (total 200 mL). The organic phase was then washed with brine and dried over anhydrous magnesium sulfate. After removal of solvent under reduced pressure and purification by column chromatography on a silica gel column with ethyl acetate:n-hexane (1:9) as eluent, the pure product (10) (3.20 g, 48%) was obtained as a colourless liquid. $^1$H-NMR (CDCl$_3$) δ(ppm): 1.24 (2×t, 6H); 2.95 (q, 4H); 4.20 (2×q, 4H); 5.80 (s, 2H) and 6.39 (s, 2H).

Example 10
5,5-Bis(2-ethoxycarbonyl-2-propenyl)-1,3-dimethyl-2,4,6 (1H,3H,5H)-pyrimidinetrione (11)

[Formula (I); $R^1=R^2=COOEt$; X, Y as N,N-dimethylbarbituric acid (1,3-dimethyl-2,4,6(1H,3H,5H)-pyrimidinetrione) ring]

To a suspension of sodium hydride (0.75 g, 80% dispersion in oil) and 1,3-dimethylbarbituric acid (1.56 g, 0.01 mol) in acetonitrile (10 mL) was added a solution of ethyl 2-(bromomethyl)propenoate (3.86 g, 0.02 mol) in acetonitrile (5 mL). The resulting mixture was allowed to stir at room temperature under nitrogen overnight. Thin layer chromatography (ethyl acetate/petroleum spirit: 1/4) indicated all the starting materials had been consumed. Water (30 mL) was added and the slightly pink solution was extracted three times with ethyl acetate (3×30 mL). The combined organic layer was washed with water, brine and then dried over anhydrous magnesium sulfate. After removal of solvent, purification by column chromatography (silica-gel 100 g, ethyl acetate:pet. spirit 40°–60° C. 1:4) gave pure product (11) (3.20 g, 84%) as a colourless liquid which solidified when stored in the freezer. $^1$H-NMR (CDCl$_3$) δ(ppm): 1.22 (t, 6H); 3.00 (s, 4H); 3.20 (s, 6H); 4.08 (q, 4H); 5.50 (s, 2H) and 6.15 (s, 2H). $^{13}$C-NMR (CDCl$_3$) δ(ppm): 13.9, 28.2, 39.9, 55.4, 61.0, 128.2, 135.2, 151.0, 166.2 and 169.9.

Example 11
5,5Bis(2-t-butoxycarbonyl-2-propenyl)-1,3-dimethyl-2,4,6 (1H,3H,5H)-pyrimidinetrione (12)

[Formula (I); $R^1=R^2=COOC(CH_3)_3$; X, Y as N,N-dimethylbarbituric acid (1,3-dimethyl-2,4,6(1 H,3H,5H)-pyrimidinetrione) ring]

To a suspension of sodium hydride (0.75 g, 80% dispersion in oil) and 1,3-dimethylbarbituric acid (1.56 g, 0.01 mol) in acetonitrile (10 mL) was added a solution of t-butyl 2-(bromomethyl)propenoate (4.42 g, 0.02 mol) in acetonitrile (5 mL). The resulting mixture was allowed to stir at room temperature under nitrogen overnight. Thin layer chromatography (ethyl acetate:petroleum spirit, 1:4) indicated all the starting materials had been consumed. Water (30 mL) was added and the slightly pink solution was extracted three times with ethyl acetate (3×50 mL). The combined organic layer was washed with water, brine and then dried over anhydrous magnesium sulfate. After removal of solvent and purification by column chromatography (silica-gel 100 g; ethyl acetate:pet. spirit 40°–60° C., 1:9) gave pure product (12) (3.02 g, 69%) as a colourless solid, m.p. 90°–91° C. $^1$H-NMR (CDCl$_3$) δ(ppm): 1.40 (s, 18H); 2.97 (s, 4H); 3.20 (s, 6H); 5.40 (s, 2H) and 6.05 (s, 2H). $^{13}$C-NMR (CDCl$_3$) δ(ppm): 27.9, 28.4, 40.1, 56.0, 74.0, 81.2, 127.4, 136.7, 151.5, 166.0 and 170.3.

Example 12
2,4,4,6-Tetrakis(t-butoxycarbonyl)-1,6-heptadiene (13)

[Formula (I); $R^1=R^2=X=Y=COOC(CH_3)_3$]

This compound was prepared using a similar procedure to that described above in Example 1. Di-t-butyl malonate and t-butyl 2-(bromomethyl)propenoate were used as starting materials. The title compound (13) was obtained as a clear liquid in 50.4% yield after column chromatography on silica-gel with ethyl acetate:petroleum spirit, 1:9 as eluent. $^1$H-NMR (CDCl$_3$) δ(ppm): 1.43 (s, 18H); 1.48 (s, 18H); 2.92 (s, 4H); 5.58 (s, 2H) and 6.15 (s, 2H).

Example 13
2,4,4,6-Tetrakis(benzyloxycarbonyl)-1,6-heptadiene (14)

[Formula (I); $R^1=R^2=X=Y=COOCH_2C_6H_5$]

This compound was prepared using a similar procedure to that described above in Example 1. Dibenzyl malonate and benzyl 2-(bromomethyl)propenoate were used as starting materials. The title compound (14) was obtained as a clear liquid in 50.5% yield after column chromatography on silica-gel with ethyl acetate:petroleum spirit, 1:4 as eluent. $^1$H-NMR (CDCl$_3$) δ(ppm): 3.06 (s, 4H); 4.97 (s, 4H); 5.11 (s, 4H); 5.67 (s, 2H); 6.29 (s, 2H) and 7.15–7.40 (m, 20H).

Example 14
2,6-Di-n-butoxycarbonyl-4,4-di-t-butoxycarbonyl-1,6-heptadiene (15)

[Formula (I); $R^1=R^2=COO(CH_2)_3CH_3$; $X=Y=COOC(CH_3)_3$]

The starting material n-butyl 2-(bromomethyl)propenoate (b.p. 81°–82° C./1.1 mmHg) was obtained by the bromination reaction of the Baylis-Hillman reaction product of n-butyl acrylate and paraformaldehyde in the presence of DABCO. $^1$H-NMR data for n-butyl 2-(bromomethyl)propenoate: δ(ppm) (CDCl$_3$) 0.93 (t, 3H); 1.40 (tq, 2H); 1.70 (tt, 2H); 4.20 (s, 2H); 4.23 (t, 2H); 5.94 (s, 1H) and 6.30 (s, 1H).

The title compound (15) was prepared using a similar procedure to that described above in Example 1, di-t-butyl malonate and n-butyl 2-(bromomethyl)propenoate were used as starting materials. The title compound (15) was obtained in 97% yield after column chromatography on silica-gel with diethyl ether:petroleum spirit, 3:17 as eluent. $^1$H-NMR (CDCl$_3$) δ(ppm): 0.93 (t, 6H, 2×CH$_2$CH$_3$); 1.38 (m, 4H, 2×CH$_2$CH$_3$); 1.43 (s, 18H, 6×CH$_3$); 1.63 (m, 4H, 2×OCH$_2$CH$_2$CH$_2$); 2.93 (s, 4H); 4.10 (t, 4H, 2×OCH$_2$CH$_2$); 5.68 (s, 2H, vinylic-H) and 6.25 (s, 2H, vinylic-H).

Example 15
4,4-Dibenzyloxycarbonyl-2,6-dicarboxy-1,6-heptadiene (16)

[Formula (I); $R^1=R^2=COOH$; $X=Y=COOCH_2C_6H_5$]

4,4-dibenzyloxycarbonyl-2,6-di-t-butoxycarbonyl-1,6-heptadiene (7) [Formula (I); $R^1=R^2=COOC(CH_3)_3$; $X=Y=COOCH_2C_6H_5$] (5.64 g, 0.01 mol) was dissolved in dichloromethane (100 mL). Formic acid (50 mL) was added and the resulting solution was heated at reflux for 43 hours. After this time, excess formic acid and the solvent were removed on a rotary evaporator. The title product (16) was isolated as a colourless solid (3.80 g, 84%) after being triturated with diethyl ether, filtered, washed twice with diethyl ether and air dried. $^1$H-NMR (DMSO-d$_6$) δ(ppm): 2.86 (s, 4H); 5.00 (s, 4H, 2×OCH$_2$); 5.63 (s, 2H, vinylic-H); 6.15 (s, 2H, vinylic-H) and 7.26 (m, 10H, ArH). $^{13}$C-NMR (DMSO-d$_6$) δ(ppm): 34.3, 56.6, 66.7, 127.9, 128.0, 128.3, 128.6, 135.2, 136.0, 167.9 and 169.5.

Example 16
4-Diethoxyphosphoryl-2,4,6-tris(ethoxycarbonyl)-1,6-heptadiene (17)

[Formula (I); $R^1=R^2=X=COOEt$; $Y=P(O)(OEt)_2$]

To a suspension of sodium hydride (3.60 g, 80% dispersion in oil) in acetonitrile (150 mL) was added a solution of triethyl phosphonoacetate (11.20 g, 0.05 mol) in acetonitrile (25 mL) at room temperature with vigorous stirring. The resulting mixture was stirred for 10 minutes before a solution of ethyl 2-(bromomethyl)propenoate (19.30 g, 0.10 mol) in acetonitrile (25 mL) was added and allowed to stir further at room temperature overnight (16 h) under nitrogen. This reaction was initially exothermic. Water (100 mL) was added, and the mixture extracted three times with diethyl ether (total 350 mL). The organic phase was then washed with brine and dried over anhydrous magnesium sulfate. After removal of solvent under reduced pressure and purification by column chromatography on a silica gel column with ethyl acetate:n-hexane, 3:1 as eluent, the pure product (17) (21.0 g, 94%) was obtained as a colourless liquid. $^1$H-NMR (CDCl$_3$) δ(ppm): 1.26 (m, 15H); 2.85 (dd, 2H); 3.06 (dd, 2H); 4.08 (m, 10H); 5.63 (s, 2H) and 6.20 (s, 2H). $^{13}$C-NMR (CDCl$_3$) δ(ppm): 13.8, 14.1, 16.2, 16.3, 34.2, 51.3, 54.1, 60.7, 61.5, 62.4, 62.6, 127.9, 136.3, 136.5, 167.1 and 170.1.

Example 17
4-Cyano-4-diethoxyphosphoryl-2,6-bis(ethoxycarbonyl)-1,6-heptadiene (18)

[Formula (I); R$^1$=R2=COOEt; X=CN; Y=P(O)(OEt)$_2$]

The title compound (18) was prepared using a similar procedure to that described above in Example 16. Diethyl cyanomethylphosphonate (8.86 g) was used instead of triethyl phosphonoacetate. The title compound (18) was obtained in 50% yield as a very pale yellow liquid after column chromatography on silica-gel with ethyl acetate:n-hexane, 1:1 as eluent. $^1$H-NMR (CDCl$_3$) δ(ppm): 1.26 (t, 6H); 1.32 (t, 6H); 2.78 (dd, 2H); 3.05 (dd, 2H); 4.20 (m, 8H); 5.90 (br. s, 2H) and 6.43 (br. s, 2H). $^{13}$C-NMR (CDCl$_3$) δ(ppm): 14.1, 16.2, 33.4, 40.9, 43.6, 61.1, 64.4, 117.7, 130.5, 134.7 and 166.4.

Example 18
4,4-Bis(diethoxyphosphoryl)-2,6-bis(ethoxycarbonyl)-1,6 heptadiene (19)

[Formula (I); R$^1$=R$^2$=COOEt; X=Y=P(O)(OEt)$_2$]

The starting material, tetraethyl methylenediphosphonate, is a colourless liquid prepared from the reaction of dibromomethane and triethyl phosphite, b.p. 132° C. (0.25 mmHg), $^1$H-NMR (CDCl$_3$) δ(ppm) 1.28 (t, 12H, 4×CH$_2$CH$_3$); 2.40 (t, 2H, PCH$_2$P) and 4.10 (m, 8H, 4×OCH$_2$), $^{13}$C-NMR (CDCl$_3$) δ(ppm) 16.2; 22.5, 25.3, 28.0 and 62.5.

To a suspension of sodium hydride (0.66 g, 80% dispersion in oil) in acetonitrile (20 mL) was added a solution of tetraethyl methylenediphosphonate (2.26 g, 0.0078 mol) in acetonitrile (5 mL) at room temperature with vigorous stirring. The resulting mixture was stirred for 10 minutes before a solution of ethyl 2-(bromomethyl)propenoate (3.86 g, 0.016 mol) in acetonitrile (5 mL) was added. The resulting mixture was then allowed to heat at 64° C. overnight (16 h) under nitrogen. After this time, water (50 mL) was added, and the mixture extracted three times with ethyl acetate (total 150 mL). The organic phase was then washed with brine and dried over anhydrous magnesium sulfate. After removal of solvent under reduced pressure and purification by column chromatography on a silica gel column, using ethyl acetate initially and gradually changing to 4% ethanol in ethyl acetate as eluent. The pure product (19) (2.40 g, 60%) was obtained as a very pale yellow liquid. $^1$H-NMR (CDCl$_3$) δ(ppm): 1.30 (t, 18H, 6×CH$_2$CH$_3$); 3.05 (t, 4H, 2×allylic-CH2); 4.14 (m, 12H, 6×OCH$_2$); 5.90 (s, 2H, vinylic-H) and 6.26 (s, 2H, vinylic-H). $^{13}$C-NMR (CDCl$_3$) δ(ppm): 14.1, 16.2, 32.2, 44.9, 47.6, 50.2, 60.6, 62.6, 127.6, 129.4, 136.5 and 167.7.

Example 19
4-Benzyloxycarbonyl-2,6-bis(ethoxycarbonyl)-4-methoxycarbonyl-1,6-heptadiene (20)

[Formula (I); R$^1$=R$^2$=COOEt; X=COOCH$_3$; Y=COOCH$_2$C$_6$H$_5$]

To a suspension of sodium hydride (1.32 g, 0.044 mol, 80% dispersion in oil) in acetonitrile (20 mL) was added a solution of benzyl methyl malonate (4.16 g, 0.02 mol) in acetonitrile (50 mL) at room temperature with vigorous stirring. The resulting mixture was stirred for 10 minutes before a solution of ethyl 2-(bromomethyl)propenoate (7.72 g, 0.04 mol) in acetonitrile (5 mL) was added and allowed to stir further at room temperature overnight (16 hr). This reaction was initially exothermic. Water (30 mL) was added, and the mixture extracted three times with ethyl acetate (total 200 mL). The organic phase was then washed with brine and dried over anhydrous magnesium sulfate. After removal of solvent under reduced pressure and purification by column chromatography on a silica gel column with ethyl acetate:n-hexane, 1:9 as eluent, the pure product (20) (6.25 g, 72.4%) was obtained as a colourless liquid. $^1$H-NMR (CDCl$_3$) δ(ppm): 1.27 (t, 6H, 2×CH$_2$CH$_3$); 2.96 (s, 4H, 2× allylic-CH$_2$); 3.58 (s, 3H, OCH$_3$); 4.14 (q, 4H, 2×OCH$_2$CH$_3$); 5.08 (s, 2H, OCH$_2$Ph); 5.65 (s, 2H, vinylic-H); 6.23 (s, 2H, vinylic-H) and 7.30 (m, 5H, ArH). $^{13}$C-NMR (CDCl$_3$) δ(ppm): 14.1, 35.0, 52.1, 57.5, 60.9, 67.0, 128.0, 128.2, 128.4, 128.8, 135.7, 135.9, 166.9, 170.0 and 170.6.

Example 20
4-Benzyloxycarbonyl-2-t-butoxycarbonyl-6-ethoxycarbonyl-4-methoxycarbonyl-1,6-heptadiene (21)

[Formula (I); R$^1$=COOC(CH$_3$)$_3$; R$^2$=COOEt; X=COOCH$_2$C$_6$H$_5$; Y=COOCH$_3$]

The title compound was prepared stepwise. In the first step, benzyl methyl malonate was reacted with an equimolar amount of ethyl 2-(bromomethyl)propenoate and sodium hydride in acetonitrile to give the product, benzyl 2-methoxycarbonyl-4-ethoxycarbonyl-pent-4-enoate, in 43% yield [$^1$H-NMR (CDCl$_3$) δ(ppm): 1.28 (t, 3H); 2.92 (d, 2H); 3.60 (s, 3H); 3.83 (t, 1H); 4.20 (q, 2H); 5.17 (s, 2H); 5.58 (s,1H); 6.18 (s, 1H) and 7.32 (m, 5H)]. In the second step, to a cooled suspension of sodium hydride (0.30 g, 0.01 mol, 80% dispersion in oil) in acetonitrile (20 mL), was added benzyl 2-methoxycarbonyl-4-ethoxycarbonyl-pent-4-enoate (2.68 g, 0.0084 mol). The resulting mixture was allowed to stir for 10 minutes before a solution of t-butyl 2-(bromomethyl)propenoate (1.85 g) in acetonitrile (5 mL) was added and stirring continued at room temperature overnight under nitrogen. After work-up, the title product (21) was obtained in 72% yield as a colourless liquid. $^1$H-NMR (CDCl$_3$) δ(ppm): 1.28 (t, 3H); 1.46 (s, 9H); 2.94 (s, 2H); 2.96 (s, 2H); 3.58 (s, 3H); 4.16 (q, 2H); 5.10 (s, 2H); 5.60 (s, 1H); 5.67 (s, 1H); 6.17 (s, 1H) and 7.32 (m, 5H).

Example 21
2,2-Bis(2-ethoxycarbonyl-2-propenyl)-5,5dimethyl-1,3-cyclohexanedione (22)

[Formula (I); R$^1$=R$^2$=COOEt; X, Y as 5,5-dimethyl-1,3-cyclohexanedione (dimedone) ring]

To a cooled suspension of sodium hydride (0.72 g, 80% dispersion in oil) in acetonitrile (20 mL) was added 5,5-dimethyl-1,3-cyclohexanedione (dimedone) (1.40 g, 0.01 mol) with vigorous stirring under nitrogen. The resulting mixture was stirred for a further 10 minutes before a solution of ethyl 2-(bromomethyl)propenoate (3.86 g, 0.02 mol) in acetonitrile (5 mL) was added and stirring continued at 4° C. for 1 hour and then at room temperature overnight (16 hours). Water (30 mL) was added, and the mixture extracted three times with ethyl acetate (total 120 mL). The organic phase was then washed with brine and dried over anhydrous magnesium sulfate. After removal of solvent under reduced pressure and purification by column chromatography on a silica gel column with ethyl acetate: n-hexane 2:3 as eluent, the pure product (22) (2.20 g, 60.4%) was obtained as a colourless liquid. $^1$H-NMR (CDCl$_3$) δ(ppm): 0.97 (s, 6H); 1.30 (t, 6H); 2.63 (s, 4H); 2.82 (s, 4H); 4.18 (q, 4H); 5.54 (s, 2H) and 6.12 (s, 2H).

Example 22
2,6-Bis(ethoxycarbonyl)-4,4-bis(phenylsulfonyl)-1,6-heptadiene (23)

[Formula (I); R$^1$=R$^2$COOEt; X=Y=SO$_2$Ph]k

Bis(phenylsulphonyl)methane (1.0 g, 3.38 mmol) was dissolved in acetonitrile (20 ml) and stirred while sodium hydride (0.233 g, 7.44 mmol) was added. The resultant suspension was stirred at room temperature for one hour, then cooled on ice while ethyl α-(bromomethyl)acrylate (1.31 g, 6.76 mmol) was added dropwise over 10 minutes. Upon completion of the addition, the mixture was allowed to warm to room temperature and stirring was continued for 3 hours. Acetonitrile was removed under reduced pressure, water added, and the product extracted with diethyl ether (3×50 ml). The combined organic phase was dried over anhydrous magnesium sulphate, filtered and evaporated under reduced pressure to give a pale yellow oil. The crude product was applied to a silica gel column and eluted with diethyl ether: petroleum spirit, 1:1. The lower R$_f$ component proved to be the desired product, and was isolated as a white solid, m.p. 112°–114° C. $^1$H-NMR (CDCl$_3$) δ(ppm): 1.20 (t,6H); 3.30 (s,4H); 4.10 (q,4H); 5.95 (s, 2H); 6.30 (s,2H); 7.50–8.05 (m, 10H).

Free Radical Cyclopolymerisation of monomer of Example 2

Free radical homopolymerisation of (2) (0.9M) was carried out in o-xylene with α,α'-azobisisobutyronitrile (AIBN) as initiator at 60° C. in the absence of oxygen. After 20 and 64 hours, the polymer was precipitated (by pouring the o-xylene solution slowly into n-hexane) and isolated as white powder in 40% and 91% yield respectively. A small portion of the polymer was examined by GPC using a Waters Instrument connected to six μ-Styragel columns (10$^{6-}$, 10$^{5-}$, 10$^{4-}$, 10$_{3-}$, 500 and 100 Å pore size) using THF as eluent at a flow rate of 1 mL/min. The results are summarised in Table 1.

TABLE 1

Cyclopolymerisation of (2) in o-xylene (0.9M) at 60° C.

| [AIBN] (mol/L) | Reaction Time (hr) | Yield (%) | M$_n$* | M$_w$* | M$_w$/M$_n$ |
|---|---|---|---|---|---|
| 0.009 | 20 | ~40 | 26,550 | 47,250 | 1.78 |
| 0.009 | 64 | 91 | 23,440 | 47,230 | 2.01 |

*Molecular weights were determined by GPC, calibrated with polystyrene standards.

The cyclopolymers are soluble in most common organic solvents such as dichloromethane, chloroform, ethyl acetate, acetone, tetrahydrofuran, toluene, o-xylene, but insoluble in n-pentane, n-hexane.

The NMR ($^1$H and $^{13}$C) analyses display no residual olefinic resonances and the spectra are consistent with the cyclic structure for the polymers given in formula II.

Differential scanning calorimetric (DSC) analysis of the above cyclopolymer showed: T$_g$ 77.4° C. (onset temperature) and T$_g$ 84.9° C. (midpoint temperature) which is somewhat higher than that of poly(ethyl methacrylate) (T$_g$ 65° C.).

The cyclopolymer was easily solvent cast onto glass plates to give a uniform and clear thin film.

Cyclopolymerisation of Monomer (2) Using 'Quasi-Living' Radical Technique

A solution of N-(2-tert-butoxy-1-phenylethoxy)-N,N-di-tert-butylamine [see: Rizzardo et al., Eur. Pat. Appl. EP 135,280 (1985)] (160.5 mg, 0.5 mmol), monomer 2,4,4,6-tetrakis(ethoxycarbonyl)-1,6-heptadiene (2) (1.92 g, 5 mmol) and o-xylene (2.5 mL) was degassed by three successive freeze-evacuate-thaw cycles and then heated at 100° C. for 1.5 hours. After this time, the reaction mixture was poured into petroleum spirit (30°–40° C.) to precipitate the cyclopolymer (0.25 g. 12% conversion) which was shown by $^1$H-NMR and GPC to consist of cyclopolymer-(2) with an average number of 12 units. GPC: M$_n$ 4,700; M$_w$ 8,015 and dispersity 1.69. The $^1$H-NMR spectrum (d 0.8–1.4) indicated the presence of di-t-butylaminoxy end groups.

Free Radical Cyclopolymerisation of Other 4,4-Disubstituted 1,6-Diene Monomers

Table 2 summarises the results of the study on AIBN-initated cyclopolymerisation of the new 1,6-dienes of the current invention over the temperature range 60° C.–90° C. The polymerisations proceeded smoothly, with no evidence of crosslinking, even at high conversion. The resulting cyclo-homopolymers are soluble in most common organic solvents.

TABLE 2

Results of cyclopolymerisation of 4,4-disubstituted 1,6-diene monomers.

| Monomer | [M] (mol/L) | [AIBN] × 10$^2$ (mol/L) | temp. (°C.)/ time (hr) | Conv. (%) | M$_n$* | D |
|---|---|---|---|---|---|---|
| (4) | 0.52 | 2.60 | 80/16 | 75.0 | 1,735 | 1.43 |
| (5) | 0.56 | 2.80 | 60/24 | ~0.5 | — | — |
| (9) | 0.56 | 0.78 | 60/65 | ~0.5 | — | — |
| (6) | 0.25 | 1.25 | 60/20 | 64.0 | 13,990 | 1.63 |
| (6) | 0.10 | 0.50 | 60/20 & 90/2 | 67.0 | 6,040 | 2.10 |
| (7) | 0.33 | 0.66 | 60/20 | 94.0 | 22,060 | 2.40 |
| (7) | 0.20 | 0.40 | 60/20 | 76.0 | 18,960 | |
| (7) | 0.09 | 0.45 | 80/20 | 56.0 | 4,790 | 1.28 |
| (7) | 0.10 | 0.50 | 80/20 & 90/2 | 58.6 | 5,750 | 1.30 |
| (10) | 0.59 | 1.08 | 62/20 & 80/4 | 90.0 | 7,600 | 3.70 |
| (11) | 0.53 | 1.06 | 60/66 | 94.5 | 1,780 | 1.25 |
| (13) | 0.20 | 0.43 | 60/66 | 94.6 | 3,300 | 1.41 |
| (15) | 0.29 | 1.45 | 70/16 | 76.3 | 8,600 | 2.29 |
| (16) | 0.16 | 0.32 | 60/64 | 95.0 | 44,200 | 1.99 |
| (17) | 0.50 | 0.50 | 60/20 | 77.0 | 39,000 | 2.17 |
| (18) | 0.43 | 0.86 | 60/64 | 96.0 | 25,200 | 5.77 |
| (19) | 0.29 | 0.59 | 60/64 | 89.3 | 2,990 | 1.18 |
| (20) | 0.37 | 0.74 | 60/64 | 92.0 | 23,500 | 3.30 |
| (23) | 0.15 | 0.15 | 60/64 | 20.0 | 2,800 | 1.41 |

*Molecular weights were determined by GPC calibrated with polystyrene standards.

Free Radical Cyclocopolymerisation of Monomer (2) and Methyl Methacrylate.

α,α'-Azobisisobutyronitrile (19.96 mg) was dissolved in freshly distilled methyl methacrylate (10.0 mL). An aliquot (2.0 mL) was removed and transferred to an ampoule containing the amount of monomer (2), shown in Table 3. The mixture was polymerised at 60° C. for one hour in the absence of oxygen. The contents of the ampoule were then diluted in ethyl acetate (2 mL) and poured into n-hexane and the precipitated cyclocopolymer was collected and dried in vacuo to constant weight. A small portion of the polymer was examined by GPC as previously described to obtain molecular weight data and polydispersities (see Table 3). From the NMR results of the cyclocopolymerisation of (2) with MMA, the monomer (2) is consumed at twice the rate of MMA.

TABLE 3

| (2) (mg) | [(2)] × 10$^2$/ [MMA] | $M_n$* | $M_w$* | $M_w/M_n$ |
|---|---|---|---|---|
| 0 | 0 | 221,570 | 462,060 | 2.08 |
| 84.5 | 1.17 | 181,080 | 306,920 | 1.69 |
| 165.8 | 2.30 | 120,000 | 218,300 | 1.82 |
| 302.3 | 4.19 | 92,320 | 161,400 | 1.75 |

*Molecular weights were determined by GPC, calibrated with polystyrene standards.

Free Radical Cyclocopolymerisation of Monomer (16) and Ethoxy Triethyleneglycol Methacrylate. (ETEGMA)

Cyclocopolymerisation of a deoxygenated mixture of monomer 4,4-dibenzyloxycarbonyl-2,6-dicarboxy-1,6-heptadiene (16) (2.26 g, 5 mmol) and ethoxy triethyleneglycol methacrylate (ETEGMA) (0.41 g, 1.67 mmol) in acetone (30 mL) using AIBN (21.8 mg, 2 mol %) as initiator was carried out at 60° C. for 20 hours. After removal of some the acetone solvent, the copolymer (2.60 g, 97%) was isolated by precipitation into n-hexane. GPC: $M_n$ 28,800; $M_w$ 68,600 and dispersity 2.38.

Free Radical Cyclocopolymerisation of Monomer (17) and Methyl Methacrylate.

A mixture of monomer, 4-diethoxyphosphoryl-2,4,6-tris (ethoxycarbonyl)-1,6-heptadiene (17) (2,10 g, 4.68 mmol), freshly distilled methyl methacrylate (MMA, 5 mL, 46.80 mmol), and AIBN (84.4 mg, 1 mol %) in ethyl acetate (20 mL) was degassed via three succesive freeze-evacuate-thaw cycles. The cyclocopolymerisation was carried out at 60° C. for 65 hours. The copolymer was obtained in quantitative yield. GPC: $M_n$ 20,600; $M_w$ 76,000 and dispersity 3.68.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

We claim:

1. A polymer or copolymer, characterized in that it contains units having the following structure:

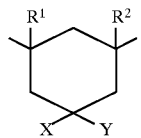

wherein:
$R^1$ and $R^2$ are independently selected from the group consisting of COOR, CN, aryl, substituted aryl, COOH, halogen, C(O)NHR$^4$, and C(O)NR$^5$R$^6$;
X and Y are independently selected from the group consisting of H, COOH, COOR, CN, R$^3$CO—, C(O)NHR$^4$, C(O)NR$^5$R$^6$, P(O)(OR$^7$)$_2$ and SO$_2$R$^8$; or X and Y together with the carbon atom to which they are attached form a carbocyclic ring system or a heterocyclic ring system containing an atom selected from the group consisting of oxygen, sulfur and nitrogen; provided X and Y are not both H; and R$^1$ and R$^2$ are not both Br when X and Y are COOC$_2$H$_5$.

2. A polymer or copolymer as claimed in claim 1 wherein the groups R$^1$ and R$^2$ are hydrophilic groups, and the groups X and Y are hydrophobic groups; or alternatively, the groups R$^1$ and R$^2$ are hydrophobic groups, and the groups X and Y are hydrophilic groups.

3. A monomer of the general formula (I)

wherein:
R$^1$ and R$^2$ are independently selected from the group consisting of COOR, CN, aryl, substituted aryl, COOH, halogen, C(O)NHR$^4$, and C(O)NR$^5$R$^6$;
X and Y are independently selected from the group consisting of H, COOH, COOR, CN, R$^3$CO—, C(O)NHR$^4$, C(O)NR$^5$R$^6$, P(O)(OR$^7$)$_2$ and SO$_2$R$^8$; or X and Y together with the carbon atom to which they are attached form a heterocyclic ring system containing an atom selected from the group consisting of oxygen, sulfur and nitrogen; provided X and Y are not both H; R$^1$ and R$^2$ are not both Br when X and Y are COOC$_2$H$_5$; and X is not phenyl-C=O when Y is hydrogen;
R is selected from the group consisting of C$_1$ to C$_{18}$ alkyl optionally substituted with a substituent selected from the group consisting of phenyl and substituted aryl;
R$^3$ is selected from the group consisting of C$_1$ to C$_6$ alkyl, C$_3$ to C$_8$ cycloalkyl, and substituted aryl;
R$^4$ is selected from the group consisting of H, C$_1$ to C$_{18}$ alkyl and C$_3$ to C$_8$ cycloalkyl;
R$^5$ and R$^6$ are independently selected from the group consisting of C$_1$ to C$_{18}$ alkyl, C$_3$ to C$_8$ cycloalkyl, aralkyl and alkaryl;
R$^7$ is selected from the group consisting of H, C$_1$ to C$_{18}$ alkyl; and
R$^8$ is selected from the group consisting of C$_1$ to C$_{18}$ alkyl, aryl and substituted aryl.

4. A method for preparing a monomer of formula I when R$^1$ and R$^2$ are different, comprising reacting approximately equimolar quantities of compounds of Formula (V) and (VI)

in the presence of an organic or inorganic base followed by reacting the product with a compound of formula (VII) in the presence of an organic or inorganic base

wherein:
R$^1$ and R$^2$ are independently selected from the group consisting of COOR, CN, aryl, substituted aryl, COOH, halogen, C(O)NHR$^4$, and C(O)NR$^5$R$^6$;

X and Y are independently selected from the group consisting of H, COOH, COOR, CN, $R^3CO-$, $C(O)NHR^4$, $C(O)NR^5R^6$, $P(O)(OR^7)_2$ and $SO_2R^8$; or X and Y together with the carbon atom to which they are attached form a carbocyclic ring system or a heterocyclic ring system containing an atom selected from the group consisting of oxygen, sulfur and nitrogen; provided X and Y are not both H and X and Y are not both Br when $R^1$ and $R^2$ are $COOC_2H_5$;

A is a reactive atom or leaving group that reacts with the $-CH_2-$ of compound (V).

5. A monomer of claim 3 wherein X and Y, together with the carbon atom to which they are attached, form a ring system which is a dimedone ring, a 1,3-dioxan-4,6-dione ring, a barbituric acid ring, a 3-alkyl-isoxazol-5(4H)-one ring or a 3-aryl-isoxazol-5(4H)-one ring.

6. A monomer of claim 3 wherein the substituted aryl group is a phenyl group, optionally substituted with one or more groups selected from alkyl, hydroxy, amino, ester, acid, acyloxy, amide, nitrile, haloalkyl, alkoxy, silyl and silyloxy.

7. Any one of the monomers:

2,4,4,6-Tetrakis(ethoxycarbonyl)-1,6-heptadiene;

2,6-Diethoxycarbonyl-4,4-di-t-butoxycarbonyl-1,6-heptadiene;

2,2-Dimethyl-5,5-bis(2-ethoxycarbonyl-2-propenyl)-1,3-dioxan-4,6-dione;

4,4-Di-t-butoxycarbonyl-2,6-diphenyl-1,6-heptadiene;

2,6-Dibenzyloxycarbonyl-4,4-di-t-butoxycarbonyl-1,6-heptadiene;

4,4-Dibenzyloxycarbonyl-2,6-di-t-butoxycarbonyl-1,6-heptadiene;

2,4,4-Tri(ethoxycarbonyl)-6-phenyl-1,6-heptadiene;

4-Cyano-2,4,6-tris(ethoxycarbonyl)-1,6-heptadiene;

5,5-Bis(2-ethoxycarbonyl-2-propenyl)-1,3-dimethyl-2,4,6(1H,3H,5H)-pyrimidinetrione;

5,5-Bis(2-t-butoxycarbonyl-2-propenyl)-1,3-dimethyl-2,4,6(1H,3H,5H)-pyrimidinetrione;

2,4,4,6-Tetrakis(t-butoxycarbonyl)-1,6-heptadiene;

2,4,4,6-Tetrakis(benzyloxycarbonyl)-1,6-heptadiene;

2,6-Di-n-butoxycarbonyl-4,4-di-t-butoxycarbonyl-1,6-heptadiene;

4,4-Dibenzyloxycarbonyl-2,6-dicarboxy-1,6-heptadiene;

4-Diethoxyphosphoryl-2,4,6-tris(ethoxycarbonyl)-1,6-heptadiene;

4-Cyano-4-diethoxyphosphoryl-2,6-bis(ethoxycarbonyl)-1,6-heptadiene;

4,4-Bis(diethoxyphosphoryl)-2,6-bis(ethoxycarbonyl)-1,6-heptadiene;

4-Benzyloxycarbonyl-2,6-bis(ethoxycarbonyl)-4-methoxycarbonyl-1,6-heptadiene;

4-Benzyloxycarbonyl-2-t-butoxycarbonyl-6-ethoxycarbonyl-4-methoxycarbonyl-1,6-heptadiene;

2,2-Bis(2-ethoxycarbonyl-2-propenyl)-5,5-dimethyl-1,3-cyclohexanedione;

2,6-Bis(ethoxycarbonyl)-4,4-bis(phenylsulfonyl)-1,6-heptadiene.

8. A polymer or copolymer derived from at least one monomer of formula (I).

9. A copolymer of claim 8 derived from at least one monomer of formula (I) and one or more monomers selected from acrylic monomers, styrenic monomers and acrylamide monomers.

* * * * *